US00PP31059P2

(12) United States Plant Patent
Van Dijk

(10) Patent No.: US PP31,059 P2
(45) Date of Patent: Nov. 12, 2019

(54) ***ANTHURIUM* PLANT NAMED 'ANTHFUWIO'**

(50) Latin Name: ***Anthurium andraeanum* L.**
Varietal Denomination: ANTHFUWIO

(71) Applicant: ANTHURA B.V., Bleiswijk (NL)

(72) Inventor: Jan Van Dijk, Bleiswijk (NL)

(73) Assignee: ANTHURA B.V., Bleiswijk (NL)

( * ) Notice: Subject to any disclaimer, the term of this patent is extended or adjusted under 35 U.S.C. 154(b) by 0 days.

(21) Appl. No.: 15/999,890

(22) Filed: Aug. 28, 2018

(51) Int. Cl.
*A01H 5/02* (2018.01)

(52) U.S. Cl.
USPC ..... Plt./365

(58) Field of Classification Search
USPC ..... Plt./365
CPC ..... A01H 5/02; A01H 6/00
See application file for complete search history.

*Primary Examiner* — Keith O. Robinson
(74) *Attorney, Agent, or Firm* — Jondle & Associates, P.C.

(57) ABSTRACT

A new *Anthurium* plant named 'ANTHFUWIO' particularly distinguished by having shiny and strongly blistered, orange, orbicular cordate and durable spathes that retain the original color for a long period of time, dark green, shiny and ovate-cordate leaves, white spadices with yellow-green tips, early and rich flowering continuously throughout the year, and a plant height of 20.0 cm to 25.0 cm is disclosed.

3 Drawing Sheets

Genus and species: *Anthurium andraeanum* L.
Variety denomination: 'ANTHFUWIO'.

BACKGROUND OF THE NEW PLANT

The present invention comprises a new and distinct variety of *Anthurium*, botanically known as *Anthurium andraeanum* L., and hereinafter referred to by the variety name 'ANTHFUWIO'. The new *Anthurium* plant is a product of a planned breeding program conducted by the inventor in Bleiswijk, the Netherlands. The objective of this breeding program was to create a new 20.0 cm to 25.0 cm height plant with shiny and strongly blistered, orange, orbicular cordate and durable spathes.

The new variety originated from a cross-pollination made in November 2010 in Bleiswijk, The Netherlands. The female parent was a red *Anthurium* pot plant designated '17399-07' (unpatented), and the male parent was a red *Anthurium* pot plant designated '20702-01' (unpatented).

A single plant was selected from the progeny of the stated cross in November 2012 and has been asexually reproduced repeatedly by tissue culture in Bleiswijk, The Netherlands over a 6-year period. The present invention has been found to retain its distinctive characteristics through successive asexual propagations.

Plant Breeder's Rights for this variety have been applied for in the European Union on Nov. 25, 2016. 'ANTHFUWIO' has not been made publicly available or sold anywhere in the world more than one year prior to the effective filing date of this application.

SUMMARY OF THE INVENTION

The following are the most outstanding and distinguishing characteristics of this new variety when grown under normal horticultural practices in Bleiswijk, The Netherlands:

1) Shiny and strongly blistered, orange, orbicular cordate spathes;
2) White spadices with yellow-green tips; and
3) Dark green, shiny and ovate-cordate leaves.

DESCRIPTION OF THE PHOTOGRAPHS

This new *Anthurium* plant is illustrated by the accompanying photographs which show the overall plant habit including blooms and foliage of the plant; the colors shown are as true as can be reasonably obtained by conventional photographic procedures. The photographs are of a 28-week old plant grown in a greenhouse in Bleiswijk, The Netherlands in May 2018. Colors in the photographs may differ from the color values cited in the detailed botanical description, which accurately describe the actual colors of the new variety.

DESCRIPTION OF THE NEW VARIETY

Figure 1:
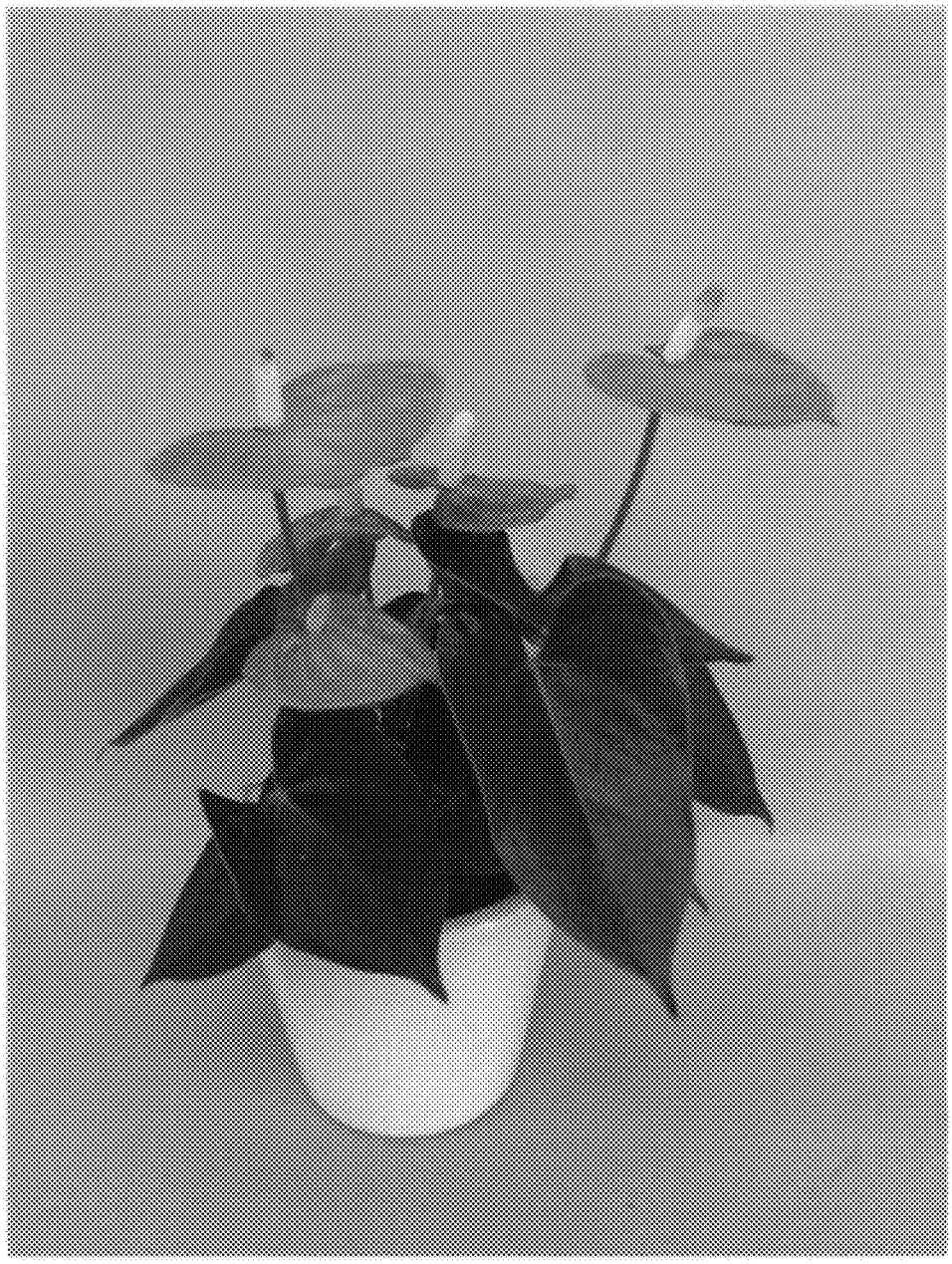
FIG. 1 shows the overall plant habit, including blooms and foliage.
Figure 2:
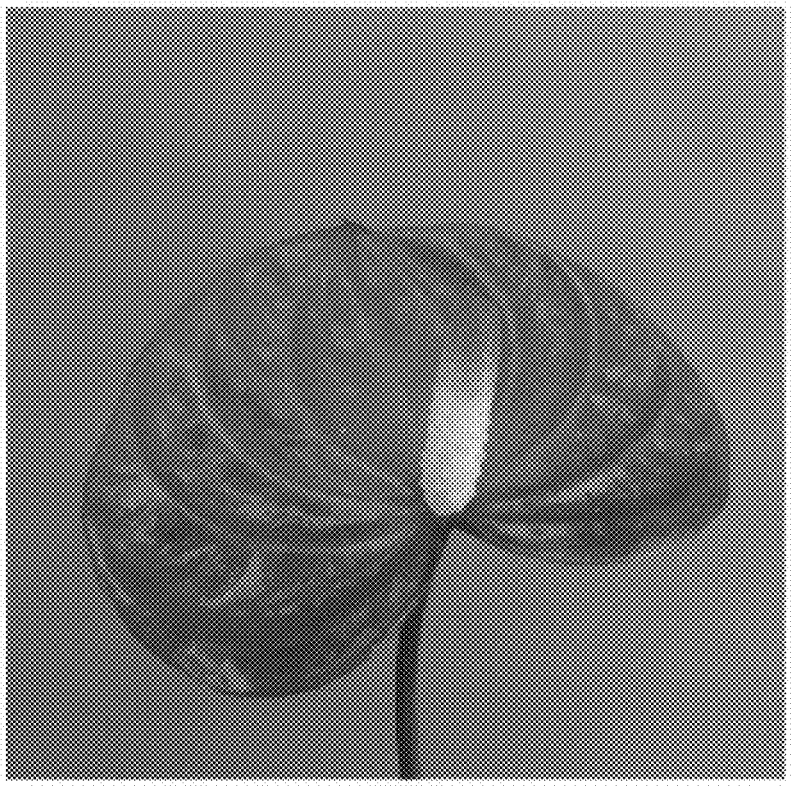
FIG. 2 shows a close-up of the mature spathe.
Figure 3:
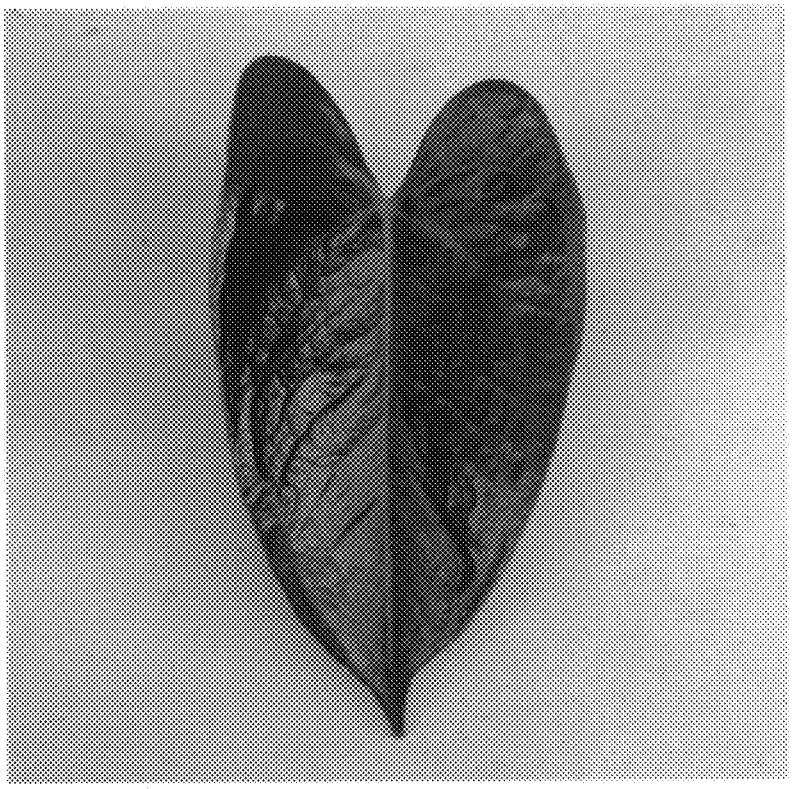
FIG. 3 shows a close-up of the upper leaf blade surface.

The following detailed description sets forth the distinctive characteristics of 'ANTHFUWIO'. The data which define these characteristics were collected from asexual reproductions carried out in Bleiswijk, The Netherlands. The plant history was taken on 28-week old plants which were planted from tissue culture in 9 centimeter (diameter) pots and grown in a glass greenhouse between 19° C. and 24° C. Observations were made in May 2018. Color readings were taken under 5000 lux natural light in the greenhouse. Color references are primarily to The R.H.S. Colour Chart of The Royal Horticultural Society of London (R.H.S.) (2015).

DETAILED BOTANICAL DESCRIPTION

Classification:
*Family*.—Araceae.
*Botanical*.—*Anthurium andraeanum* L.

*Common name.*—*Anthurium.*

*Denomination.*—'ANTHFUWIO'.

Parentage:

*Female parent.*—*Anthurium* plant '17399-07' (unpatented).

*Male parent.*—*Anthurium* plant '20702-01' (unpatented).

Plant:

*Propagation.*—Tissue culture.

*Root description.*—Fleshy-creamy (RHS 158D) with a touch of light pink (RHS 39D) colored roots with small hairy lateral roots having small greenish-yellow (between RHS 8A and 8B) colored root tips.

*Time to produce a finished flowering plant.*—28 to 30 weeks after planting in a 9 cm (diameter) pot.

*Growth habit.*—Upright.

*Height (measured from soil, including inflorescence).*—20.0 cm to 25.0 cm.

*Width (measured from leaf tips).*—17.0 cm to 20.0 cm.

Leaves:

*Immature leaves.*—Length: 7.0 cm to 9.0 cm. Width: 5.0 cm to 6.0 cm. Color: Upper surface: RHS 146A. Lower surface: RHS 146B. Texture (both upper and lower surfaces): Shiny.

*Mature leaves.*—Length (fully expanded): 10.0 cm to 12.0 cm. Width: 6.5 cm to 7.5 cm. Shape: Ovate-cordate. Apex: Acuminate. Base: Cordate. Leaf blade angle with the petiole: Between 80 degrees and 100 degrees. Leaf margin: Entire. Color: Upper surface: RHS 147A. Lower surface: RHS 146A. Texture: Shiny, leathery and thick. Venation: Pinnate veining; the mid-vein and primary veins (the veins that radiate out from the junction of petiole and leaf) protrude at the underside of the leaf blade. Venation color: Upper surface: RHS 144A. Lower surface: RHS 144B.

*Lobes.*—Present. Arrangement: Leaf blade has two lobes extending past the petiole. The lobes are non-touching. Length of lobes of mature leaf blades: 0.5 cm to 1.5 cm. Width of lobes of mature leaf blades: 2.0 cm to 3.0 cm. Distance from petiole/leaf junction to highest point on lobes of mature leaf: 2.0 cm to 3.0 cm.

*Petiole.*—Cross-section: Round. Diameter: 0.2 cm to 0.3 cm. Length: 9.0 cm to 12.0 cm for a mature leaf size. Color: Mature leaf: RHS 144B. Immature leaf: RHS 144A. Cataphyll color surrounding the petiole: Outside: RHS 176C. Inside: RHS 177D.

*Geniculum.*—Length: 1.5 cm to 2.0 cm. Width: 0.2 cm to 0.3 cm. Color: RHS 144A.

Inflorescence:

*Arrangement.*—Single.

*Flowering habit (length of flowering season).*—Continuous.

*Number of inflorescences per plant.*—6 to 8.

*Fragrance.*—Absent.

*Longevity of inflorescence on plant.*—Over a year.

Spathe:

*Buds.*—The spathe is tightly rolled around the spadix and extrudes from the peduncle sheath. After the spathe is fully open, the peduncle elongates some extra centimeters.

*Arrangement.*—Spathe angle with the peduncle is between 85 degrees and 100 degrees; the spathe stands on a wiry peduncle about 4.0 cm to 7.0 cm above the foliage.

*Shape.*—Orbicular cordate.

*Apex.*—Mucronate.

*Base.*—Cordate.

*Texture.*—Shiny and strongly blistered.

*Margin.*—Undulated.

*Size.*—Length: 5.5 cm to 6.5 cm. Width: 7.5 cm to 8.5 cm.

*Lobes.*—Present.

*Arrangement.*—The spathe has two lobes extending past the peduncle. The lobes are non-touching. Length: 1.0 cm to 1.5 cm. Width: 3.0 cm to 3.5 cm.

*Color.*—Just fully open: Upper surface: RHS 42C. Lower surface: RHS 42D. This orange color remains for a very long period, at least more than 30 weeks after opening.

Peduncle:

*Shape.*—Erect.

*Cross-section.*—Round.

*Length.*—14.0 cm to 19.0 cm.

*Diameter.*—0.2 cm to 0.3 cm.

*Color.*—RHS 144A.

Flowering time:

*General.*—One small, rooted, untreated tissue culture plant of 8.0 cm tall will flower, depending on the season, after 28 to 30 weeks and 6 to 7 blossoms appear. More blossoms appear after some additional weeks so that a full flowering and commercial plant will have 7 to 8 orange spathes. Smaller blossoms may occur on immature plants.

Spadix:

*Size.*—Length: 2.0 cm to 2.5 cm (depending on flower size). Width (at apex): 0.5 cm to 0.6 cm. Width (at base): 0.6 cm to 0.7 cm.

*Shape.*—Columnar.

*Angle from spadix tip to peduncle.*—140 degrees to 150 degrees.

*Curvature of the longitudinal axis.*—Straight.

*Texture.*—When the spathe is unfurling the spadix is smooth. When the spadix matures, small stigmata protrude. The stigmata are evenly distributed around the spadix. The spadix matures from base to top, slowly giving the spadix a somewhat rough appearance.

*Color.*—Immature: RHS 14A and RHS N144A toward the tip. Mature: RHS 158C. Ages to: RHS 153C.

Flowers:

*Quantity per spadix.*—60 to 100.

*Spadix flower arrangement.*—Bisexual, rounded in cross-section.

*Shape.*—Rounded.

*Size.*—Length: 0.05 cm to 0.10 cm. Diameter (maximum): 0.10 cm.

*Color.*—RHS 158A.

Reproductive organs:

*Stamens.*—Not visible.

*Pollen amount.*—Absent.

*Pistil.*—Quantity: 60 to 100. Length: Less than 0.01 cm. Color: RHS 158A.

*Style.*—Not observed to date.

*Stigma.*—Shape: Ovoid. Diameter: Less than 0.01 cm. Color: RHS 158A.

*Ovary*.—Rarely visible.

*Ovary color*.—Not measured.

Fruit and seed set: None observed to date.

COMPARISON WITH PARENTAL AND COMMERCIAL VARIETIES

'ANTHFUWIO' differs from the female parent plant '17399-07' (unpatented) in that 'ANTHFUWIO' has orange spathes and ovate-cordate leaves, whereas '17399-07' has red spathes and elliptical leaves.

'ANTHFUWIO' differs from the male parent plant '20702-01' (unpatented) in that 'ANTHFUWIO' has orange spathes, whereas '20702-01' has red spathes. Additionally, 'ANTHFUWIO' has a narrower angle of the spadix tip with the peduncle than '20702-01'.

'ANTHFUWIO' differs from similar commercial variety 'ANTHABAZAL' (unpatented) in that 'ANTHFUWIO' has outer cataphyll colored RHS 176C and strongly blistered spathes, whereas 'ANTHABAZAL' has cataphyll colored RHS 144B and blistered spathes.

'ANTHFUWIO' differs from similar commercial variety 'ANTHEQIBO' (U.S. Plant Pat. No. 28,190) in that 'ANTHFUWIO' has ovate-cordate leaves, strongly blistered spathes and outer cataphyll colored RHS 176C, whereas 'ANTHEQIBO' has long cordate leaves, blistered spathes and outer cataphyll colored RHS N144D. Additionally, 'ANTHFUWIO' has shorter leaves than 'ANTHEQIBO'.

I claim:

1. A new and distinct variety of *Anthurium* plant named 'ANTHFUWIO', substantially as illustrated and described herein.

* * * * *